United States Patent

Baronnet et al.

[11] 4,268,511
[45] May 19, 1981

[54] 3-AMINO(1H,3H)QUINAZOLINE-2,4-DIONE DERIVATIVES AND THEIR THERAPEUTIC APPLICATIONS

[75] Inventors: René Baronnet, Garches; Raymond Callendret, Le Pecq, both of France

[73] Assignee: Berri-Balzac, Suresnes, France

[21] Appl. No.: 130,176

[22] Filed: Mar. 11, 1980

[51] Int. Cl.³ .................. A61K 31/47; C07D 239/80; C07D 413/04
[52] U.S. Cl. .................. 424/248.57; 424/251; 544/116; 544/285; 544/94; 544/164
[58] Field of Search ................ 544/285, 116; 424/251, 424/248.57

[56] References Cited

U.S. PATENT DOCUMENTS

| | | | |
|---|---|---|---|
| 3,718,648 | 2/1973 | Beyerle et al. | 544/285 |
| 3,819,630 | 6/1974 | Parcell | 544/285 |
| 3,932,409 | 1/1976 | Konzel et al. | 544/284 |

FOREIGN PATENT DOCUMENTS

| | | | |
|---|---|---|---|
| 1485847 | 6/1967 | France | 544/285 |
| 48-1674 | 1/1973 | Japan | 544/285 |

*Primary Examiner*—Anton H. Sutto
*Assistant Examiner*—James H. Turnipseed
*Attorney, Agent, or Firm*—Young & Thompson

[57] ABSTRACT

This invention relates to compounds having the formula:

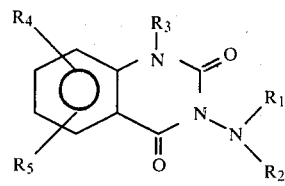

in which $R_1$ and $R_2$ are independently hydrogen, a $C_{1-4}$ alkyl group or an aliphatic or aromatic acyl group, provided $R_1$ and $R_2$ are not simultaneously hydrogen, or, together with the nitrogen atom to which they are attached, $R_1$ and $R_2$ form a 5- or 6-membered ring which may carry another heteroatom; $R_3$ is a $C_{1-4}$ alkyl group; and $R_4$ and $R_5$ represent independently a hydrogen or halogen atom, a $C_{1-4}$ alkyl group or a $C_{1-4}$ alkoxy group; and the acid addition salts of the above compounds. Said new compounds have an anxiolytic and diuretic action, together with a spasmolytic action of non-α-adrenalytic nature on the unstriated muscle fibers.

9 Claims, No Drawings

3-AMINO(1H,3H)QUINAZOLINE-2,4-DIONE DERIVATIVES AND THEIR THERAPEUTIC APPLICATIONS

This invention relates to new 3-amino(1H,3H-)quinazoline-2,4-dione derivatives, to a process for their preparation and to their therapeutic applications, typically as anxiolytic and diuretic agents, and also as spasmolytic agents of non-α-adrenalytic nature on the unstriated muscle fibers.

The new compounds of this invention have the formula:

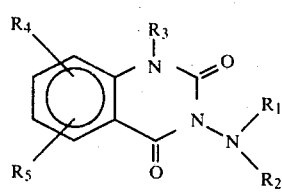
(I)

in which $R_1$ and $R_2$ represent independently a hydrogen atom, a $C_{1-4}$ alkyl group or an aliphatic or aromatic acyl group, provided $R_1$ and $R_2$ are not simultaneously hydrogen, or, together with the nitrogen atom to which they are attached, $R_1$ and $R_2$ form a 5- or 6-membered heterocycle which may carry another heteroatom; $R_3$ is a $C_{1-4}$ alkyl group; and $R_4$ and $R_5$ represent independently a hydrogen or halogen atom, a $C_{1-4}$ alkyl group or a $C_{1-4}$ alkoxy group.

The invention includes also within its scope the acid addition salts of the above-compounds (typically with hydrochloric acid, hydrobromic acid, sulfuric acid, and the like).

Said new compounds have an anxiolytic action and a diuretic action, together with a spasmolytic action of non-α-adrenalytic nature on the unstriated muscle fibres, and are thus useful in the treatment of hypertension. In addition, they are useful as synthetic intermediates.

This invention relates also to a process for the preparation of the above defined compounds, comprising reacting an anthranilic acid having the formula:

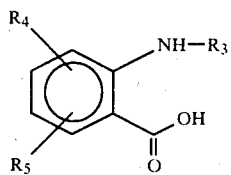
(II)

in which $R_3$, $R_4$ and $R_5$ have the aforesaid meanings, with phosgene, to give an isatoic anhydride of the formula:

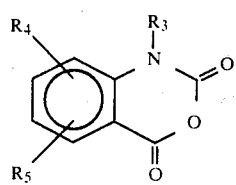
(III)

which is then reacted with a hydrazine of the formula:

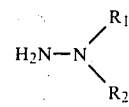
(IV)

in which $R_1$ and $R_2$ have the aforesaid meanings, to give an anthranilic hydrazide of the formula:

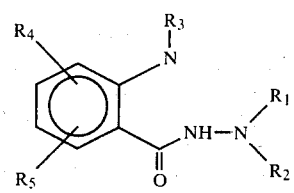
(V)

which is then cyclized with phosgene or ethyl chloroformate, to give the compound of the formula (I).

The process of this invention may be schematically illustrated as follows:

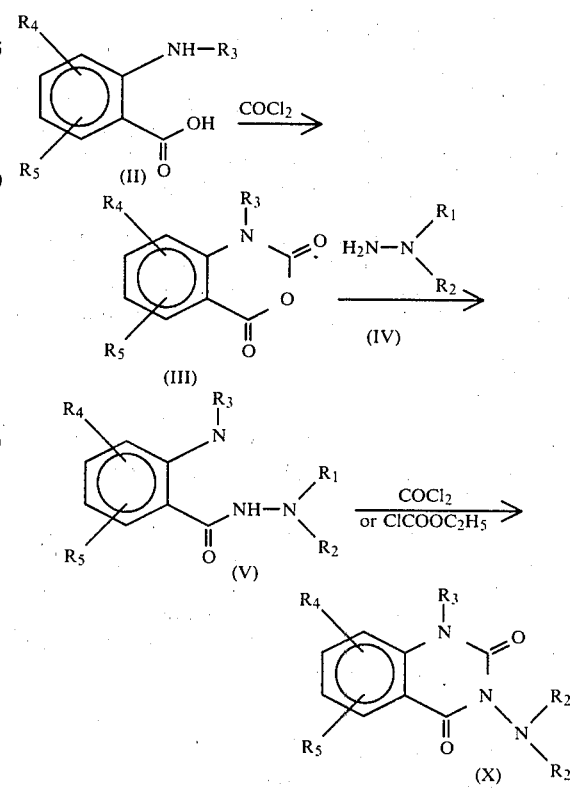

According to a modification, to obtain the compounds in which $R_1$ and $R_2$ are both acyl, the corresponding compound in which one of the symbols $R_1$ and $R_2$ is an acyl group is used as starting material and is reacted with an acylating agent to introduce the second acyl group.

The process of this invention is typically effected in the following manner:

GENERAL PRODUCTION PROCESS (a) Preparation of isatoic anhydride of the formula (III)

The suitably substituted anthranilic acid (II) is dissolved in an aqueous hydrochloric acid solution or, if desired, in dioxane when said acid is not soluble in acidic medium. A carbonyl chloride (phosgene) stream is passed through this solution. Isatoic anhydride (III) precipitates out gradually. After a contact time of 1.5 hour, the product is suction filtered, rinsed with water and dried in an oven at 100° C. The mother-liquors may be submitted to the action of a second contact with phosgene, to give another crystallization crop.

(b) Preparation of anthranilic hydrazide of the formula (V)

To a suspension in an aliphatic alcohol, or preferably in an ethylene glycol alkyl ether, typically ethylene glycol dimethyl ether, of 1 mole isatoic anhydride (III) is added 1 mole hydrazine (IV). The mixture is allowed to react until there is no more carbon dioxide evolved. The solvent is partly removed under reduced pressure and the reaction product is generally crystallized by addition of benzene. The purity of the product is sufficient for the subsequent step.

(c) Cyclization of anthranilic hydrazides (V) to (1H,3H)quinazoline-2,4-diones of the formula (I)

Method A:

The pydrazide (V) obtained in (b) is dissolved in a minimum amount of 2 N hydrochloric acid. The solution is then treated with carbonyl chloride. The reaction product precipitates out slowly from the medium. After a contact time of 1 hour, the resulting material is suction filtered, rinsed with water and dried. It is purified by recrystallization from ethanol or isopropanol.

Method B:

The hydrazide (V) is cyclized to 3-amino(1H,3H-)quinazoline-2,4-dione by refluxing the product in the presence of ethyl chloroformate for 3–4 hours. Excess ethyl chloroformate is removed by distillation and the residue is crystallized from ethanol.

The following non-limiting Examples illustrate the process of this invention.

EXAMPLE 1

Preparation of 6,7-dimethoxy-isatoic anhydride 49.5 g 2-amino-4,5-dimethoxy-benzoic anhydride are dissolved in 1 litre 2 N hydrochloric acid. A phosgene stream is passed through the stirred mixture for 1.5 hour while maintaining the temperature below 40° C. The reaction mixture is purged with a stream of air and the resulting precipitate is filtered, washed with water and dried in an oven at 100° C. M.P.=291° C.

EXAMPLE 2

Preparation of 2-amino-N-morpholinobenzamide 33 g isatoic anhydride are suspended in 200 cc ethanol heated to 70° C.; 20.5 g 4-amino-morpholine are slowly added thereto. After completion of the addition, the temperature is maintained at the same level until carbon dioxide is no longer evolved. The ethanol is partly removed (100 cc) and the reaction product is crystallized by addition of 100 cc benzene. It may be purified by recrystallization from a benzene-ethanol mixture. M.P.=172° C.

EXAMPLE 3

Preparation of 6-chloro-3-morpholino(1H,3H)quinazoline-2,4-dione (cyclization with phosgene)

23.5 g 2-Amino-5-chloro-N-morpholinobenzamide are dissolved in 500 cc 2N hydrochloric acid. A phosgene stream is passed through the solution for 1 hour. When the reaction is complete, the equipment is purged, after which the resulting material is suction filtered and washed with water. It is purified by crystallization from ethanol, M.P.=335° C.

EXAMPLE 4

Preparation of p-methoxy-3-benzoylamino(1H,3H)quinazoline-2,4-dione (cyclization with phosgene)

28.5 g N-(2-amino-benzoyl)-N'-p-methoxy-benzoyl-hydrazine are dissolved in 800 cc 2N hydrochloric acid. A phosgene stream is passed through the solution, for a period of time of 1 hour. After purging the apparatus, the reaction product is suction filtered and washed with water. It is purified by recrystallization from isopropanol. M.P.=289° C.

EXAMPLE 5

Preparation of 3-dimethylamino-1-methyl(1H,3H)quinazoline-2,4-dione (cyclization with ethyl chloroformate)

19.3 g 2-methylamino-N-dimethylaminobenzamide are refluxed in 100 cc ethyl chloroformate for 4 hours. Excess ethyl chloroformate is distilled off and the residue is crystallized from ethanol. M.P.=154° C. This compound is assigned reference number 76 089 hereinafter.

EXAMPLE 6

Preparation of 3-diacetylamino(1H,3H)quinazoline-2,4-dione 4 g 3-N-acetylamino(1H,3H)quinazoline-2,4-dione are refluxed for 5 hours in 200 cc acetic anhydride. Excess acetic anhydride is then distilled off under reduced pressure. The resulting residue is crystallized from benzene. M.p.=210° C.

The following compounds of the formula (I) were prepared in the same manner as above:

3-diethylamino-1-methyl(1H,3H)quinazoline-2,4-dione, M.P. 178° C.

3-dimethylamino-1-ethyl(1H,3H)quinazoline-2,4-dione, M.P. 98° C.

7-chloro-3-dimethylamino-1-ethyl(1H,3H)quinazoline-2,4-dione, M.P. 143° C.

7-chloro-3-dimethylamino-1-isopropyl(1H,3H)quinazoline-2,4-dione, M.P. 100° C.

This invention relates also to a therapeutic composition having in particular an anxiolytic and diuretic action, and also a spasmolytic action of non-α-adrenalytic nature on the unstriated muscle fibres, comprising, as active ingredient, a compound of above defined formula (I) or a therapeutically administrable acid addition salt thereof.

The active ingredient is generally formulated together with a suitable pharmaceutically administrable carrier.

The results of toxicological and pharmacological tests reported below illustrate the activities of the compounds of this invention.

A—TOXICITY

Acute toxicity was determined in Swiss mice. For example, for compound 76 089 the $LD_{50}$ is 250 mg/kg by the i.p. route and 225 mg/kg by the oral route.

B—DIURETIC ACTION

The diuretic action is determined in non-anaesthetized rats treated with 25 or 50 mg/kg test material administered orally or intraperitoneally, and given an i.p. injection of isotonic sodium chloride solution at the beginning of the test. The rats are used in groups of 3 animals each, and the experiments are repeated by crossing the groups of rats.

The diuresis is expressed by the percent mean increase of the diuresis with respect to the mean value obtained with the control animals.

The results obtained are given in Table I below, for compound 76 089:

TABLE I

|  | Diuresis dosage (mg/kg) | | | |
| --- | --- | --- | --- | --- |
|  | i.p. | | per os | |
|  | 25 | 50 | 25 | 50 |
| Compound 76 089 | 60 | 200 | 77 | 200 |

C—SEDATIVE ACTION

The sedative action is measured by a sedation index. This sedation index takes into account, in mice, the decrease of the exploration of the perforated board with respect to a group of control animals, the hypothermia, the mobility, the agility. The results obtained with compound 76 089 are given in Table II:

TABLE II

| Sedation index | | | Chemical sedation |
| --- | --- | --- | --- |
| 100 mg/kg i.p. | 50 mg/kg per os | 100 mg/kg per os | index 100 mg/kg p.o. |
| 236 | 76 | 164 | 179 |

On the other hand, a potentiation of psychotropic drugs such as Nembutal, Chlorpromazine, morphine, and an antagonism with respect to amphetamine should be noted. For example, compound 76 089 potentiates the hypnotic effect of Nembutal by a factor of +146%, that of Chlorpromazine by a factor of +50% and that of morphine by a factor of 40%. In contrast, it antagonizes the effects of amphetamine by a factor of 70%.

Thus, the compounds of the formula (I) have "anxiolytic" type sedative activities on the central nervous system.

They are particularly applicable to the treatment of hypertension.

The compounds of the formula (I) are typically administrable by the oral and rectal routes.

For such routes of administration, the compounds of the formula (I) are advantageously formulated in unit dosage form such as tablets, capsules, suppositories, and the like, in which the active ingredient is combined with the usual suitable pharmaceutically acceptable excipients and carriers.

Each unit dose contains advantageously 5-30 mg active ingredient.

A table formulation is given below for illustrative purposes.

| | |
| --- | --- |
| 3-Dimethylamino-1-methyl(1H,3H) quinazoline-2,4-dione | 10 mg |
| Excipient, sufficient for a tablet weighing | 150 mg |

We claim:
1. A compound selected from the compounds having the formula:

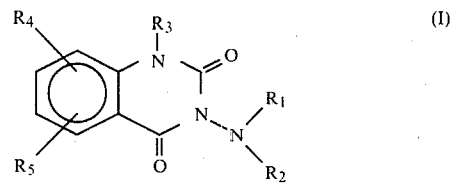

in which $R_1$ and $R_2$ represent independently from each other a member of the group selected from a hydrogen atom, a $C_{1-4}$ alkyl group, an acetyl group and a benzoyl group, $R_1$ and $R_2$ not being simultaneously hydrogen, and, when taken together with the nitrogen atom to which they are attached, $R_1$ and $R_2$ may form a morpholino radical; $R_3$ represents a $C_{1-4}$ alkyl; and $R_4$ and $R_5$ represent independently a member of the group selected from a hydrogen atom, a halogen atom, a $C_{1-4}$ alkyl group and a $C_{1-4}$ alkoxy group; and the therapeutically acceptable acid addition salts of the above compounds.

2. 3-Dimethyl-amino-1-methyl(1H,3H)quinazoline-2,4-dione.

3. 3-Diethylamino-1-methyl(1H,3H)quinazoline-2,4-dione.

4. 3-Dimethylamino-1-ethyl(1H,3H)quinazoline-2,4-dione.

5. 7-Chloro-3-dimethylamino-1-ethyl(1H,3H)quinzoline-2,4-dione.

6. 7-Chloro-3-dimethylamino-1-isopropyl(1H,3H)quinazoline-2,4-dione.

7. Therapeutic composition, having particularly an anxiolytic and diuretic action, and also a spasmolytic action of non-α-adrenalytic nature on the unstriated muscle fibres, comprising a therapeutically effective amount of a compound selected from the compounds having the formula:

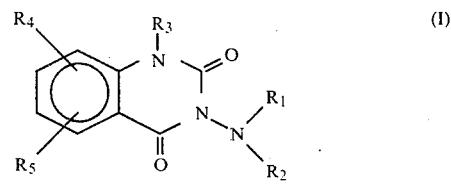

in which $R_1$ and $R_2$ represent independently from each other a member of the group selected from a hydrogen atom, a $C_{1-4}$ alkyl group, an acetyl group and a benzoyl group, $R_1$ and $R_2$ not being simultaneously hydrogen, and, when taken together with the nitrogen atom to which they are attached, $R_1$ and $R_2$ may form a morpholino radical; $R_3$ represents a $C_{1-4}$ alkyl; and $R_4$ and $R_5$ represent independently a member of the group selected from a hydrogen atom, a halogen atom, a $C_{1-4}$ alkyl group and a $C_{1-4}$ alkoxy group; and the therapeutically acceptable acid addition salts of the above compounds, together with a pharmaceutically acceptable carrier.

8. Therapeutic composition as claimed in claim 7, in unit dosage form for oral administration.

9. Therapeutic composition as claimed in claim 7, in unit dosage form for parenteral administration.

* * * * *